United States Patent [19]

Lang

[11] 3,962,268

[45] June 8, 1976

[54] PROCESS FOR PRODUCING 2:2'- OR 4:4'-BIPYRIDYLS

[75] Inventor: George Henry Lang, Manchester, England

[73] Assignee: Imperial Chemical Industries Limited, London, England

[22] Filed: May 2, 1975

[21] Appl. No.: 574,089

[30] Foreign Application Priority Data
May 22, 1974 United Kingdom............... 22890/74
Nov. 15, 1974 United Kingdom............... 49487/74

[52] U.S. Cl............................................. 260/296 D
[51] Int. Cl.² ....................................... C07D 213/02
[58] Field of Search ................................ 260/296 D

[56] References Cited
UNITED STATES PATENTS
3,882,133  5/1975  Dalton ........................... 260/296 D

OTHER PUBLICATIONS

Klingsberg, Pyridine and its Derivatives, Part 2, p. 437, Interscience Pub., (1961).

Primary Examiner—Alan L. Rotman
Attorney, Agent, or Firm—Cushman, Darby & Cushman

[57] ABSTRACT

A process for the manufacture of 2:2'- or 4:4'-bipyridyls which comprises heating a 2- or 4-(halo-magnesium)-pyridine respectively with a halogen or the halide of an element from groups 4b, 5b, 6b, 7b, 8, 1b, 2b, 3a, 4a and 5a of the Periodic table. Typically the process involves heating grignard reagents from 2- or 4-bromo pyridine with bromine or silver copper or cobalt chlorides or bromides at 40° to 130°C.

Bipyridyls are useful as intermediates for herbicide manufacture.

6 Claims, No Drawings

PROCESS FOR PRODUCING 2:2'- OR 4:4'-BIPYRIDYLS

The present invention relates to chemical processes in particular to processes for the manufacture of 2:2' and 4:4' bipyridyls.

According to the present invention there is provided a process for the manufacture of 2:2' - or 4:4-bipyridyls which comprises heating a 2- or 4-(halomagnesium)-pyridine respectively with a halogen or the halide of an element from groups 4b, 5b, 6b, 7b, 8, 1b, 2b, 3a, 4a and 5a of the Periodic Table.

By Periodic Table we mean the tabulation of chemical elements as set out on page B-3 of "The Handbook of Chemistry and Physics" 54th Edition 1973–1974 published by CRC Press of Cleveland Ohio.

The 2- or 4-(halomagnesium) pyridines used in the process of the present invention are compounds of a type known collectively as "Grignard reagents" or as "Grignard compounds." The formation of these compounds can take place by an conventional method of forming Grignard compounds, such as reacting 2- or 4-halo-pyridines with magnesium. Such reactions are usually carried out in solvents e.g. diethyl, ether, tetrahydrofuran, di-n-butyl ether, anisole, ethylene glycol dimethyl ether and di-amyl ether.

As examples of 2-(halomagnesium) pyridines which may be used in the process of the present invention there may be mentioned 2-(chloromagnesium) pyridine and 2-(chloromagnesium)-4-methylpyridine, and especially useful are 2-(bromomagnesium)pyridines such as 2-(bromomagnesium)pyridine and 2-(bromomagnesium)-4-methylpyridine.

As examples of 4-(halomagnesium)pyridines which may be used in the process of the present invention there may be mentioned 4-(chloromagnesium)pyridine and 4-(chloromagnesium)-2-methylpyridine, and especially useful are 4-(bromomagnesium)pyridines and 4-(bromomagnesium)pyridine and 4-(bromomagnesium)-2-methylpyridine.

The 2- or 4-(halomagnesium) pyridines may be isolated or purified, for example, by removal of solvent before being subjected to the process of the present invention but it usually most convenient to proceed without such isolation or purification.

The 4-halopyridines which may be used to form the 4-(halomagnesium)pyridines are often not stable materials, when in the free form, hence they are normally stored as derivatives e.g. as salts such as hydrochlorides. The preparation of 4-(halomagnesium)pyridines thus normally involves liberating free 4-halopyridines e.g. by neutralising salt shortly before reaction with the magnesium or generating it in situ in the reaction mixture.

The process of heating the 2- or 4-(halomagnesium)-pyridines with a halogen or halide of an element from groups 4b, 5b, 6b, 7b, 8, 1b, 2b, 3a, 4a and 5a of the Periodic Table can take place at any temperature from 40° to 180°C but temperatures of 50° to 130°C are preferred.

Additional solvents may be added to the solutions of 2- or 4-(halomagnesium) pyridines prepared for use in the process of the present invention. Examples of such solvents are chlorobenzene, toluene and xylene. Where low boiling point ethers such as diethyl ether are used to prepare the Grignard reagent the additional solvent may be a higher boiling point ether such as tetrahydrofuran, ethylene glycol dimethyl ether or anisole.

As examples of elements from the specified groups of the Periodic Table whose halides are particularly suited for use in the present process there may be mentioned silver, copper and cobalt.

These elements may be employed as halides in any valency state when more than one exists, for example, copper may be used as either cuprous or cupric halide.

The halides of the elements from groups 4b, 5b, 6b, 7b, 8, 1b, 2b, 3a, 4a and 5a of the Periodic Table may be from any halogen but chlorides and bromides are preferred.

Any halogen, that is, fluorine, chlorine bromine or iodine may be used in the process of the invention but bromine is particularly preferred.

The halides of the specified elements or halogen may be added to the reaction mixture in any convenient manner, for example, gaseous halogens may be bubbled into the reaction mixture and solid halides may be added as a suspension, preferably in a finely divided form, in a solvent. It is often beneficial to agitate the reaction mixture during the process of the present invention.

The halides of the specified elements or halogen are normally employed in amounts of from 1 to 4 moles especially from 1 to 2 moles of per mole of 2- or 4-(halomagnesium)pyridine.

The 2:2'- and 4:4'-bipyridyls made by the process of the present invention may be isolated and purified by any conventional procedure such as washing, evaporation, steam distillation and fractional distillation.

The process of the present invention may be used to manufacture various 2:2'-bipyridyls such as 4:4'-dimethyl-2:2'-bipyridyl, but it is especually preferred to manufacture 2:2'-bipyridyl by the process of the present invention.

The process of the present invention may be used to manufacture various 4:4'-bipyridyls such as 2:2'-dimethyl-4:4'-bipyridyl, but it is especially preferred to manufacture 4:4'-bipyridyl by the process of the present invention.

The 2:2' and 4:4'-bipyridyls manufactured by the process of the present inventions are particularly useful as intermediates for the manufacture of other products especially for the manufacture of herbicides.

The invention is illustrated by the following examples in which all parts and percentages are by weight unless otherwise specified.

EXAMPLE 1

Dry magnesium turnings (2.4 parts) are covered with 20 parts sodium-dry diethyl ether in a flask fitted with a stirrer thermometer and reflux condenser heated/cooled in a water bath. Ethyl bromide (3.5 parts) and a crystal of iodine are added to initiate the reaction with the magnesium turnings. Immediately this occurs, 2-bromopyridine (8 parts) is added and the whole is stirred for 2½ hours. Chlorobenzene (50 parts) and silver bromide (9.4 parts) are added and the reaction mixture is stirred at 60°C for 3 hours. After standing overnight, the mixture is made alkaline with caustic soda and is steam distilled after adding 100 parts of water. 2:2-Bipyridyl collects in the distillate in an amount equal to 2.4 parts (by analysis of the ferrous complex, equivalent to 55.3% yield based on the 2.bromopyridine charged). The 2:2'bipyridyl is recovered from the aqueous distillate by extraction with chloroform.

EXAMPLES 2–14

By using the general procedure detailed in example 1 further examples of the manufacture of 2:2'-bipyridyl can be carried out using in place of the 9.4 parts of silver bromide, other halides as detailed in the following table.

TABLE 1

| Reagent | Parts | Reaction Temp °C | Conditions Time hr. | 2:2'Bipyridyl p.b.w. (% theory yield) | Example No. |
| --- | --- | --- | --- | --- | --- |
| Silver Bromide | 18.8 | 82 | 3 | 2.4 parts (60.5) | 2 |
| Silver Bromide | 6.0 | 60 | 9 | 0.9 (23.3) | 3 |
| Cuprous Chloride | 10.0 | 64 | 9 | 2.0 (51.4) | 4 |
| Cupric Chloride | 13.4 | 60 | 8 | 1.9 (47.1) | 5 |
| Cobalt Chloride | 3.5 | 56 | 3 | 1.4 (35.1) | 6 |
| Nickel Chloride | 6.5 | 65 | 3 | 0.7 (18.1) | 7 |
| Ferrous Chloride | 12.6 | 60 | 9 | 0.3 (8.1) | 8 |
| Lead Chloride | 27.8 | 60 | 3 | 0.4 (9.2) | 9 |
| Zinc Chloride | 12.6 | 60 | 3 | 0.3 (7.3) | 10 |
| Ferric Chloride* | 16.2 | 60 | 2 | 0.2 (4.8) | 11 |
| Mercuric Chloride | 27.0 | 60 | 3 | 0.05 (4.3) | 12 |
| Cadmium Chloride | 18.3 | 60 | 3 | 0.1 (0.6) | 13 |
| Bromine | 4.0 | 60 | 10 | 0.8 (20.8) | 14 |

*Used in butyl ether as solvent, in place of the diethyl ether in example 1.

EXAMPLE 15

Proceeding as described in example 1 but using 2-chloropyridine (5.7 parts) instead of 2-bromopyridine and heating for a period of 10 hours at 60°C there is obtained a yield of 2:2-bipyridyl formed of 1.0 parts (25.4% yield theory).

EXAMPLES 16–21

By using the general procedure detailed in Example 1 the following examples of the manufacture of 2:2'-bipyridyl can be carried out by using in place of the diethyl ether and chlorobenzene various solvents as detailed in the table below.

EXAMPLE 22

Dry magnesium turnings (4.8 parts) are covered with 25 parts of sodium dry ether in a flask fitted with a stirrer, thermometer and reflux condenser and positioned in a water bath for heating/cooling. Ethyl bromide (1.4 parts) and a crystal of iodine are added to initiate the reaction with the magnesium turnings. When this occurs, 4-bromopyridine hydrochloride (4.0 parts) and ethyl bromide (3.0 parts) are added simultaneously and the whole stirred under reflux for 3 hours. At the end of this time chlorobenzene (50 parts) and anhydrous silver bromide (9.4 parts) are added and the reaction mixture is stirred at reflux temperature for a further 18 hours. The mixture is made slightly acid (pH 6–7) with hydrochloric acid, filtered and extracted with ether. The resultant ether solution contains 4:4'-bipyridyl (0.26 parts) equivalent 16.4% theory yield (based on 4-bromopyridine hydrochloride added). It can be isolated from the solution by conventional means.

TABLE 2

| Solvent | | Reaction Conditions for reaction with silver bromide | | | | |
| --- | --- | --- | --- | --- | --- | --- |
| for Grignard formation* | | Added for reaction with silver bromide. | | Temp °C | Time hr. | 2:2'Bipyridyl p.b.w. (% theory yield) | Example No. |
| Name | Amount | Name | Amount | | | | |
| Ethyl ether | 50 | Chloro-benzene | 50 | 60 | 2 | 2.2 (55.3) | 16 |
| n-butyl ether | 20 | chloro-benzene | 50 | 84 | 9 | 1.4 (35.4) | 17 |
| Anisole | 45 | None | — | 70 | 9 | 1.0 (25.9) | 18 |
| n-butyl ether | 45 | None | — | 70 | 9 | 1.8 (44.7) | 19 |
| Tetrahydrofuran | 45 | None | — | 70 | 9 | 1.0 (24.7) | 20 |
| Tetrahydrofuran | 24 | Chloro-benzene | 50 | 75 | 9 | 3.2 (41.0) | 21 |

*8 parts of 2-bromopyridine used except for example 21 which uses 16 parts

EXAMPLE 23

The procedure detailed in Example 1 is followed using an equivalent amount of 4-chloropyridine hydrochloride in place of the 4-bromopyridine hydrochloride. The final ether extract is shown by gas-liquid chromatographic analysis to contain 4:4'-bipyridyl.

EXAMPLE 24

Proceeding as described in Example 1 using anhydrous cupric chloride (6.7 parts) instead of the silver bromide (9.4 parts), the final ether extract is shown by gas-liquid chromatographic analysis to contain 4:4'-bipyridyl.

EXAMPLE 25

Proceeding as described in Example 1 using anhydrous cobalt chloride (6.5 parts) instead of the silver bromide (9.4 parts), the final ether extract is shown by gas-liquid chromatographic analysis to contain 4:4'-bipyridyl.

We claim:

1. A process for the manufacture of 2:2'- or 4:4'-bipyridyls which comprises heating at 40°–180°C. in an organic solvent selected from hydrocarbons, halogenated hydrocarbons and ethers a 2- or 4-(halo-magnesium)-pyridine respectively with from 1 to 4 moles of the halide of an element from groups 4b, 5b, 6b, 7b, 8, 1b, 2b, 3a, 4a and 5a of the Periodic table.

2. A process as claimed in claim 1 using one to two moles of halogen or halide of an element from the specified groups of the Periodic table per mole of (halo-magnesium)-pyridine.

3. A process as claimed in claim 1 in which the halo-magnesium-pyridine is a chloro-magnesium-pyridine.

4. A process as claimed in claim 1 in which the halo-magnesium-pyridine is a bromo-magnesium-pyridine.

5. A process as claimed in claim 1 in which the halo-magnesium-pyridine is heated with the chloride or bromide of an element from the specified groups of the Periodic table.

6. A process as claimed in claim 1 in which the element from the specified groups of the Periodic table is silver, copper or cobalt.

* * * * *